(12) United States Patent
Harris

(10) Patent No.: US 6,864,350 B2
(45) Date of Patent: *Mar. 8, 2005

(54) SOLUBLE, DEGRADABLE POLY (ETHYLENE GLYCOL) DERIVATIVES FOR CONTROLLABLE RELEASE OF BOUND MOLECULES INTO SOLUTION

(75) Inventor: J. Milton Harris, Huntsville, AL (US)

(73) Assignee: Nektar Therapeutics AL, Corporation, Huntsville, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/318,322

(22) Filed: Dec. 12, 2002

(65) Prior Publication Data

US 2003/0220447 A1 Nov. 27, 2003

Related U.S. Application Data

(60) Continuation of application No. 09/824,297, filed on Apr. 2, 2001, now Pat. No. 6,515,100, which is a division of application No. 08/937,846, filed on Sep. 25, 1997, now Pat. No. 6,214,966.
(60) Provisional application No. 60/026,716, filed on Sep. 26, 1996.

(51) Int. Cl.$^7$ ..................... A61K 31/74; A61K 31/765; A61K 47/48; C08G 73/10
(52) U.S. Cl. ................. 528/322; 424/78.08; 424/78.17; 424/78.19
(58) Field of Search ....................... 528/322; 424/78.08, 424/78.17, 78.19, 85.1, 85.7

(56) References Cited

U.S. PATENT DOCUMENTS

| | | | |
|---|---|---|---|
| 4,179,337 A | 12/1979 | Davis et al. | |
| 4,670,417 A | 6/1987 | Iwasaki et al. | |
| 4,766,106 A | * 8/1988 | Katre et al. | 514/12 |
| 5,476,653 A | 12/1995 | Pitt et al. | |
| 5,672,662 A | 9/1997 | Harris et al. | |
| 5,720,950 A | 2/1998 | Poiani et al. | |
| 5,730,990 A | 3/1998 | Greenwald et al. | |
| 5,738,846 A | * 4/1998 | Greenwald et al. | 424/85.7 |
| 5,840,900 A | 11/1998 | Greenwald et al. | |
| 6,214,966 B1 | * 4/2001 | Harris | 528/322 |
| 6,515,100 B2 | * 2/2003 | Harris | 528/322 |

OTHER PUBLICATIONS

Greenwald et al., "Highly Water Soluble Taxol Derivatives: 7-Polythylene Glycol Carbamates and Carbonates",*J. Org. Chem.*, 1995, pp. 331-336, vol. 60, No. 2.

(List continued on next page.)

*Primary Examiner*—Thurman K. Page
*Assistant Examiner*—Blessing Fubara
(74) *Attorney, Agent, or Firm*—Alston & Bird LLP

(57) ABSTRACT

PEG and related polymer derivatives having weak, hydrolytically unstable linkages near the reactive end of the polymer are provided for conjugation to drugs, including proteins, enzymes, small molecules, and others. These derivatives provide a sufficient circulation period for a drug-PEG conjugate and then for hydrolytic breakdown of the conjugate and release of the bound molecule. In some cases, drugs that previously had reduced activity when permanently coupled to PEG can have therapeutically suitable activity when coupled to a degradable PEG in accordance with the invention. The PEG of the invention can be used to impart water solubility, size, slow rate of kidney clearance, and reduced immunogenicity to the conjugate. Controlled hydrolytic release of the bound molecule in the aqueous environment can then enhance the drug delivery system.

44 Claims, 3 Drawing Sheets

OTHER PUBLICATIONS

Harris, J. Milton, "Introduction to Biotechnical and Biomedical Applications of Poly(Ethylene Glycol)",*Poly(Ethylene Glycol) Chemistry: Biotechnical and Biomedical Applications*, 1992, pp. 1–14, Plenum Press, New York.

Torchilin et al., "Amphiphilic Polyethylene Glycol Derivatives: Long–Circulating Micellar Carriers for Therapeutic and Diagnositc Agents",*Polymer Preprints*, 1997, pp. 545–546, vol. 38, No. 1.

Zalipsky et al., "Attachment of Drugs to Polyethylene Glycols",*Eur. Polym. J.*, 1983, pp. 1177–1183, vol. 19, No. 12.

* cited by examiner

SOLUBLE, DEGRADABLE POLY(ETHYLENE GLYCOL) DERIVATIVES FOR CONTROLLABLE RELEASE OF BOUND MOLECULES INTO SOLUTION

CROSS REFERENCE TO RELATED APPLICATION

This application is a continuation of U.S. application Ser. No. 09/824,297, filed Apr. 2, 2001, now U.S. Pat. No. 6,515,100 B2, which is a divisional application of U.S. application Ser. No. 08/937,846, filed Sep. 25, 1997, now U.S. Pat. No. 6,214,966 B1, which is related to commonly owned copending Provisional Application Ser. No. 6/026,716, filed Sep. 26, 1996, and claims the benefit of its earlier filing date under U.S.C 119(e), all of which are incorporated by reference herein.

FIELD OF THE INVENTION

This invention relates to active derivatives of poly(ethylene glycol) and related hydrophilic polymers with a reactive moiety at one end of the polymer chain suitable for chemical coupling to another molecule.

BACKGROUND OF THE INVENTION

Chemical attachment of the hydrophilic polymer poly(ethylene glycol)(PEG), which is also known as poly(ethylene oxide) (PEO), to molecules and surfaces is of great utility in biotechnology. In its most common form PEG is a linear polymer terminated at each end with hydroxyl groups:

$$HO-CH_2CH_2O-(CH_2CH_2O)_n-CH_2CH_2-OH$$

This polymer can be represented in brief form as HO-PEG-OH where it is understood that the -PEG- symbol represents the following structural unit:

$$-CH_2CH_2O-(CH_2CH_2O)_n-CH_2CH_2-$$

In typical form n ranges from approximately 10 to approximately 2000.

PEG is commonly used as methoxy-PEG-OH, or mPEG, in which one terminus is the relatively inert methoxy group, while the other terminus is a hydroxyl group that is subject to ready chemical modification.

$$CH_3O-(CH_2CH_2O)_n-CH_2CH_2-OH \quad mPEG$$

PEG is also commonly used in branched forms that can be prepared by addition of ethylene oxide to various polyols, such as glycerol, pentaerythritol and sorbitol. For example, the four-arm, branched PEG prepared from pentaerythritol is shown below:

$$C(CH_2-OH)_4 + n\ C_2H_4O \rightarrow C[CH_2O-(CH_2CH_2O)_n-CH_2CH_2-OH]_4$$

The branched polyethylene glycols can be represented in general form as R(-PEG-OH)$_n$ in which R represents the central "core" molecule, such as glycerol or pentaerythritol, and n represents the number of arms.

PEG is a well known polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, Greenwald, Pendri and Bolikal in *J. Org. Chem.*, 60, 331–336 (1995) have shown that the water-insoluble drug taxol, when coupled to PEG, becomes water soluble. In related work, Davis et al. in U.S. Pat. No. 4,179,337 have shown that proteins coupled to PEG have enhanced blood circulation lifetime because of reduced rate of kidney clearance and reduced immunogenicity. Hydrophobic proteins have been described that gain increased water solubility upon coupling to PEG. These applications and many leading references are described in the book by Harris (J. M. Harris, Ed., "Biomedical and Biotechnical Applications of Polyethylene Glycol Chemistry," Plenum, N.Y., 1992).

To couple PEG to a molecule such as a protein or on a surface, it is necessary to use an "activated derivative" of the PEG having a functional group at the terminus suitable for reacting with some group on the surface or on the protein (such as an amino group). Among the many useful activated derivatives of PEG is the succinimidyl "active ester" of carboxymethylated PEG as disclosed by K. Iwasaki and Y. Iwashita in U.S. Pat. No. 4,670,417. This chemistry can be illustrated with the active ester reacting with amino groups of a protein (the succinimidyl group is represented as NHS and the protein is represented as PRO-NH$_2$):

$$PEG\text{-}O-CH_2-CO_2\text{-}NHS + PRO\text{-}NH_2 \rightarrow PEG\text{-}O-CH_2-CO_2-NH\text{-}PRO$$

Problems have arisen in the art. Some of the functional groups that have been used to activate PEG can result in toxic or otherwise undesirable residues when used for in vivo drug delivery. Some of the linkages that have been devised to attach functional groups to PEG can result in an undesirable immune response. Some of the functional groups do not have appropriate selectivity for reacting with particular groups on proteins and can tend to deactivate the proteins.

Attachment of a PEG derivative to a substance can have a somewhat unpredictable impact on the substance. Proteins, small drugs, and the like can have less biological activity when cojugated with a PEG derivative. For others, activity is increased.

Another example of a problem that has arisen in the art is exemplified by the succinimidyl succinate "active ester" mPEG-SS (the succinimidyl group is represented as NHS):

$$CH_3O-PEG-OH \longrightarrow$$
$$mPEG$$
$$CH_3O-PEG-O_2C-CH_2CH_2-CO_2-NHS$$
$$mPEG\text{-}SS$$

The mPEG-SS active ester is a useful compound because it reacts rapidly with amino groups on proteins and other molecules to form an amide linkage (—CO—NH—). A problem with the mPEG-SS active ester, which was recognized by K. Iwasaki and Y. Iwashita in U.S. Pat. No. 4,670,417, is that this compound possesses an ester linkage in the backbone that remains after coupling to an amine such as a protein (represented as PRO-NH$_2$):

$$mPEG\text{-}SS + PRO\text{-}NH_2 \rightarrow mPEG\text{-}O_2C-CH_2CH_2-CONH\text{-}PRO$$

The remaining ester linkage is subject to rapid hydrolysis and detachment of PEG from the modified protein. Too rapid hydrolysis can preclude use of a PEG derivative for many applications. Several approaches have been adopted to solve the problem of hydrolytic instability. For example, mPEG succinimidyl carbonate has been proposed, which contains only ether linkages in the polymer backbone and reacts with proteins to form a conjugate that is not subject to hydrolysis.

It would be desirable to provide alternative PEG derivatives that are suitable for drug delivery systems, including delivery of proteins, enzymes, and small molecules, or for other biotechnical uses. It would also be desirable to provide alternative PEG derivatives that could enhance drug delivery systems or biotechnical products.

SUMMARY OF THE INVENTION

The invention provides chemically active polyethylene glycols and related polymers that are suitable for coupling to other molecules to give water-soluble conjugates, and in which the linkage between the polymer and the bound molecule is subject to predetermined cleavage for controlled delivery of the bound molecule into the surrounding environment.

The PEG and related polymer derivatives of the invention contain weak, hydrolytically unstable linkages near the reactive end of the polymer that provide for a sufficient circulation period for a drug-PEG conjugate and then hydrolytic breakdown of the conjugate d release of the bound molecule. Methods of preparing the active PEGs and related polymers, PEG conjugates, and methods of preparing the PEG conjugates are also included in the invention.

The PEG and related polymer derivatives of the invention are capable of imparting water solubility, size, slow rate of kidney clearance, and reduced immunogenicity to the conjugate, while also providing for controllable hydrolytic release of the bound molecule into the aqueous environment by design of the linkage. The invention can be used to enhance solubility and blood circulation lifetime of drugs in the blood stream and then to deliver a drug into the blood stream substantially free of PEG. In some cases, drugs that previously had reduced activity when permanently conjugated to PEG can have therapeutically suitable activity when coupled to a degradable PEG in accordance with the invention.

In general form, the derivatives of the invention can be described by the following equations:

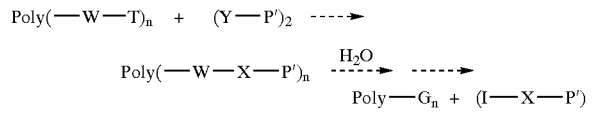

In the above equations,

"Poly" is a linear or branched polyethylene glycol of molecular weight from 300 to 100,000 daltons. Poly can also be a related nonpeptidic polymer as described in the Detailed Description;

n is the number of chemically active end groups on Poly and is the number of molecules that can be bound to Poly;

W is a hydrolytically unstable weak group;

T is a reactive group;

$(Y-P')_n$ represents a molecule for conjugation to Poly, in which Y is a reactive group that is reactive with T and P' is the portion of the molecule that is to be bound and released, including, for example, a peptide P' in which Y is an amine moiety and T is a PEG activating moiety reactive with amine moieties;

X is the new linkage formed by reaction of Y and T; and

G and I are new groups formed by hydrolysis of W.

Examples of hydrolytically unstable groups W include carboxylate esters, phosphate esters, acetals, imines, orthoesters, peptides and oligonucleotides. T and Y are groups reactive toward each other. There are many examples of such groups known in organic chemistry. Some examples include active esters reacting toward amines, isocyanates reacting toward alcohols and amines, aldehydes reacting toward amines, epoxide reacting toward amines, and sulfonate esters reacting toward amines. Examples of P' include peptide, oligonucleotide and other pharmaceuticals. Examples of X include amide from reaction of active esters with amine, urethane from reaction of isocyanate with hydroxyl, and urea from reaction of amine with isocyanate. Examples of G and I are alcohol and acid from hydrolysis of carboxylate esters, aldehyde and alcohol from hydrolysis of acetals, aldehydes and amine from hydrolysis of imines, phosphate and alcohol from hydrolysis of phosphate esters, amine and acid from hydrolysis of peptide, and phosphate and alcohol from hydrolysis of oligonucleotides.

An example of the invention is shown in the following equation for conjugation of methoxy-PEG-OH (mPEG) with a peptide drug and for hydrolytic release of the peptide drug. The weak linkage W in the conjugate is an ester group.

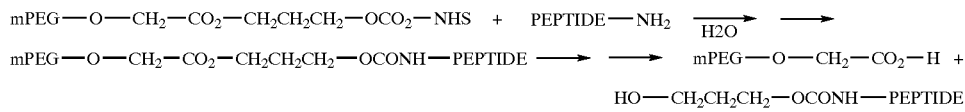

The released peptide contains no mPEG. The released peptide contains an additional short molecular fragment, which is sometimes called a "tag" and is the portion of the linkage opposite the PEG from the hydrolytically unstable linkage.

Thus, the invention provides hydrolytically unstable linkages in activated PEGs and related polymers that are suitable for controlled delivery of drugs from conjugation with the PEG to the surrounding environment. Several types of linkages, including ester linkages, are suitable for use in the invention. However, the ester linkages of the invention, in contrast to mPEG-SS and mPEG-SG, provide for variation and control of the rate of hydrolytic degradation.

The foregoing and other objects, advantages, and features of the invention, and the manner in which the same are accomplished, will be more readily apparent upon consideration of the following detailed description of the invention taken in conjuntion with the accompanying drawings, which illustrates an exemplary embodiment.

BRIEF DESCRIPTION OF THE DRAWINGS

FIG. 1 is 1 day. FIG. 2 is 8 days. FIG. 3 is 14 days.

DETAILED DESCRIPTION

Figure 1:
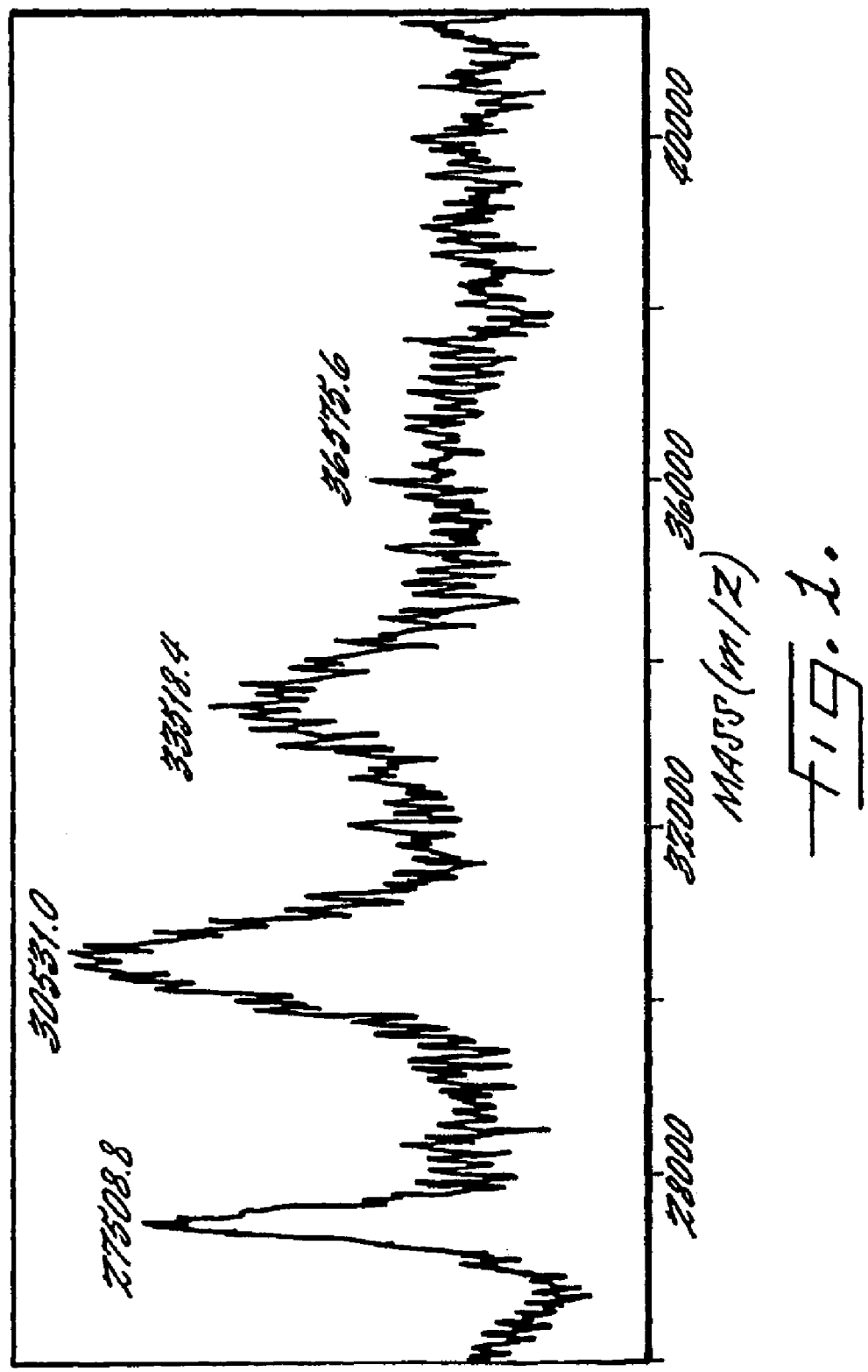
FIGS. 1 through 3 are illustrations of MALDI-MS spectra of the molecular weight distribution of an mPEG-HBA and subtilisin conjugate at different times after preparation.

The following detailed description describes various examples of the derivatives of the invention as described by the following general equations presented in the summary:

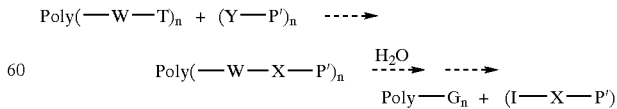

In the discussion below, Poly will often be referred to for convenience as PEG or as poly(ethylene glycol). However, it should be understood that other related polymers are also suitable for use in the practice of the invention and that the use of the term PEG or poly(ethylene glycol) is intended to be inclusive and not exclusive in this respect.

Poly(ethylene glycol) is useful in the practice of the invention. PEG is used in biological applications because it has properties that are highly desirable and is generally approved for biological or biotechnical applications. PEG typically is clear, colorless, odorless, soluble in water, stable to heat, inert to many chemical agents, does not hydrolyze or deteriorate, and is nontoxic. Poly(ethylene glycol) is considered to be biocompatible, which is to say that PEG is capable of coexistence with living tissues or organisms without causing harm. More specifically, PEG is not immunogenic, which is to say that PEG does not tend to produce an immune response in the body. When attached to a moiety having some desirable function in the body, the PEG tends to mask the moiety and can reduce or eliminate any immune response so that an organism can tolerate the presence of the moiety. Accordingly, the activated PEGs of the invention should be substantially non-toxic and should not tend substantially to produce an immune response or cause clotting or other undesirable effects.

Other water soluble polymers than PEG are suitable for similar modification. These other polymers include poly (vinyl alcohol) ("PVA"); other poly(alkylene oxides) such as poly(propylene glycol) ("PPG") and the like; and poly (oxyethylated polyols) such as poly(oxyethylated glycerol), poly(oxyethylated sorbitol), and poly(oxyethylated glucose), and the like. The polymers can be homopolymers or random or block copolymers and terpolymers based on the monomers of the above polymers, straight chain or branched, or substituted or unsubstituted similar to mPEG and other capped, monofunctional PEGs having a single active site available for attachment to a linker.

Specific examples of suitable additional polymers include poly(oxazoline), poly(acryloylmorpholine) ("PAcM"), and poly(vinylpyrrolidone) ("PVP"). PVP and poly(oxazoline) are well known polymers in the art and their preparation and use in the syntheses described for mPEG should be readily apparent to the skilled artisan. PAcM and its synthesis and use are described in U.S. Pat. Nos. 5,629,384 and 5,631,322, the contents of which are incorporated herein by reference in their entirety.

It should be understood that by "drug" is meant any substance intended for the diagnosis, cure, mitigation, treatment, or prevention of disease in humans and other animals, or to otherwise enhance physical or mental well being. The invention could be used for delivery of biologically active substances generally that have some activity or function in a living organism or in a substance taken from a living organism.

The terms "group," "functional group," "moiety," "active moiety," "reactive site," and "radical" are all somewhat synonymous in the chemical arts and are used in the art and herein to refer to distinct, definable portions or units of a molecule and to units that perform some function or activity and are reactive with other molecules or portions of molecules.

The term "linkage" is used to refer to groups that normally are formed as the result of a chemical reaction and typically are covalent linkages. Hydrolytically stable linkages means that the linkages are stable in water and do not react with water at useful pHs for an extended period of time, potentially indefinitely. Hydrolytically unstable linkages are those that react with water, typically causing a molecule to separate into two or more components. The linkage is said to be subject to hydrolysis and to be hydrolyzable. The time it takes for the linkage to react with water is referred to as the rate of hydrolysis and is usually measured in terms of its half life.

The invention includes poly(ethylene glycols) containing ester groups as weak linkages and succinimidyl esters as reactive groups useful for coupling to amine-containing molecules to be delivered in vivo or into a substance taken from a living entity:

PEG-W-$CO_2$-NHS

Where W=—$O_2C$—$(CH_2)_n$—O— n=1–5
—O—$(CH_2)_n$—$CO_2$—$(CH_2)_m$— n=1–5, m=2–5
—O—$(CH_2)_n$—$CO_2$—$(CH_2)_m$—O— n=1–5, m=2–5

The invention includes poly(ethylene glycols) containing ester groups as weak linkages and isocyanates as reactive groups useful for coupling to amine- and alcohol-containing molecules:

PEG-W-N=C=O

Where W=—O—$(CH_2)_n$—$CO_2$—$(CH_2)_m$— n=1 to 5, m=2 to 5

The invention includes poly(ethylene glycols) containing acetal groups as weak linkages and succinimidyl esters as reactive groups useful for coupling to amine-containing molecules:

PEG-W-$CO_2$-NHS

For example where W=

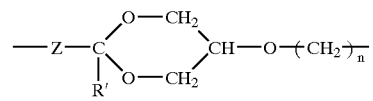

or where W=

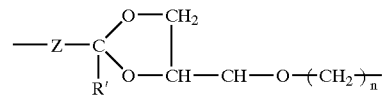

and where n=1–10,
Z=—O—$C_6H_4$— and —O—$(CH_2)_m$—$CH_2$— m=1–5
R'=alkyl or H

The invention includes poly(ethylene glycols) containing imine groups as weak linkages and succinimidyl esters as reactive groups useful for coupling to amine-containing molecules:

PEG-W-$CO_2$-NHS

Where W=-Z-CH=N—$(CH_2)_m$—O— m=1–5
and where Z=—O—$C_6H_4$—
and —O—$(CH_2)_m$—$CH_2$— m=1–5

The invention also includes poly(ethylene glycols) containing phosphate ester groups as weak linkages and succinimidyl esters as reactive groups useful for coupling to amine-containing molecules:

PEG-W-$CO_2$-NHS

Where W=—$(CH_2)_n$—$OPO_3$—$(CH_2)_m$— n and m=1–5

The invention includes poly(ethylene glycols) containing ester-linked amino acids as weak linkages and succinimidyl esters as reactive groups useful for coupling to amine-containing molecules. An advantage of this derivative is that hydrolytic breakdown leaves a biologically acceptable amino acid attached to the released molecule:

PEG-W-$CO_2$-NHS

Where W=—O—$(CH_2)_n$—$CO_2$—$(CH_2)_m$—CH(NH-t-Boc)- n=1–5, m=1–5 t-Boc=$(CH_3)_3$C—O—CO—

The invention includes poly(ethylene glycols) containing peptides as weak linkages and succinimidyl esters as reactive groups useful for coupling to amine-containing molecules. An advantage of this derivative is that hydrolytic breakdown leaves a usually biologically acceptable peptide fragment attached to the released molecule:

PEG-W-$CO_2$-NHS

Where W=—CO(NH—CHR—CO)$_n$—NH—CHR— n=2–20

R=the set of substituents typically found on α-amino acids

The invention includes poly(ethylene glycols) containing oligonucleotides as weak linkages and succinimidyl esters as reactive groups useful for coupling to amine-containing molecules. An advantage of this derivative is that hydrolytic breakdown leaves the biologically acceptable oligonucleotide fragment attached to the released molecule:

PEG-W-$CO_2$-NHS

Where W=oligonucleotide

It should also be recognized that branched activated PEGs can be prepared in accordance with the invention having weak linkages near the reactive end of the polymer for controlled hydrolytic degradation. Suitable branched PEGs can be prepared in accordance with U.S. Pat. No. 5,932,462, the contents of which are incorporated herein in their entirety by reference. These branched PEGs can then be modified in accordance with the present teachings.

The invention is illustrated with respect to several specific examples below, including determination of hydrolysis half lives for specific derivatives.

EXAMPLES

Example 1

Preparation of $CH_3O$-PEG-O—$(CH_2)_n$—COO—$CH_2$—COOH (n=1: mPEG-CM-GA-NHS, and n=2: mPEG-PA-GA-NHS)

Reactions:

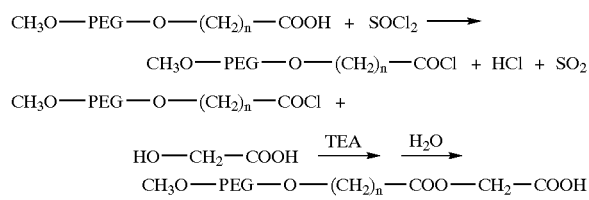

$CH_3O$-PEG-O—$(CH_2)_n$—COOH 3000 (3.0 g, 1 mmole, mPEG-CM or mPEG-PA) was azeotropically dried with 60 ml of toluene under $N_2$. After two hours, the solution was cooled to room temperature, and thionyl chloride solution (2 ml, 4 mmole) in $CH_2CL_2$ was injected. The solution was stirred at room temperature overnight. The solvent was condensed on a rotary evaporator and the residual syrup was dried in vacuo for about four hours over $P_2O_5$ powder. Glycolic acid (0.2 g, 2.7 mmole) was azeotropically distilled with 70 ml of 1,4-dioxane and the distillation was stopped when approximately 20 ml of solution remained. The solution was slowly cooled to room temperature under $N_2$. The glycolic acid/dioxane solution was then added to the dried PEG acyl chloride. After the PEG was dissolved, 0.6 ml of dry triethylamine was injected to the system (precipitate formed immediately) and the solution was stirred overnight. The salt was removed by filtration and the filtrate was condensed on a rotary evaporator at 55° C. and dried in vacuo. The crude product was then dissolved in 100 ml of distilled water and the pH of the solution was adjusted to 3.0. The aqueous phase was extracted three times with a total of 80 ml of methylene chloride. The combined organic phase was dried over sodium sulfate, filtered to remove salt, condensed on a rotary evaporator, and added to 100 ml of ethyl ether. The precipitate was collected by filtration and dried in vacuo. Yield 2.55 g (85%). $^1$H NMR (DMSO-$d_6$): δ 3.5 (br m, PEG), 4.3–4.6 (s, PEGCOOC$\underline{H}_2$COOH), 2.59 (t, PEGOCH$_2$C$\underline{H}_2$COO (PA)), 4.19 (s, PEGOC$\underline{H}_2$COO (CM)).

Example 2

Preparation of HOOC—$CH_2$—OOC—$CH_2$—O-PEG-O—$CH_2$—COO—$CH_2$—COOH

Reactions:

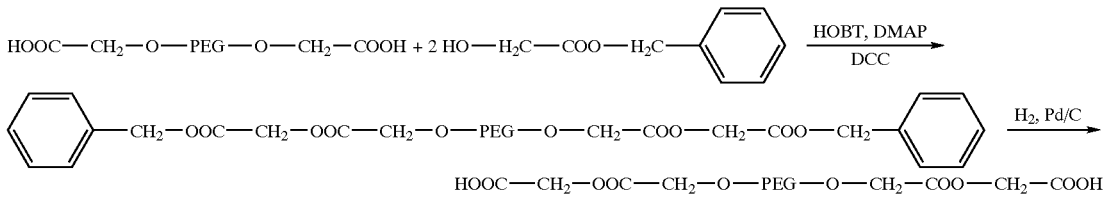

Difunctional carboxymethyl PEG-ester benzyl glycolate 20,000: Difunctional carboxymethyl PEG 20,000 (4 gram, 0.4 mmole acid group), benzyl glycolate (0.6 mmole), dimethylaminopyridine (0.44 mmole), 1-hydroxybenzotriazole (0.4 mmole) and dicyclohexylcarbodiimide (0.56 mmole) were dissolved in 40 ml of methylene chloride. The solution was stirred at room temperature under $N_2$ overnight. The solvent was then removed under vacuum and the resulting residue was added to 20 ml of toluene at 40° C. The undissolved solid was removed by filtration and the filtrate was added to 200 ml of ethyl ether. The precipitate was collected by filtration and dried in vacuo. Yield 4 gram (100%). $^1$H NMR(DMSO-$d_6$): δ 3.5 (br m, PEG), 4.81 (s, PEGCOOC$\underline{H}_2$COOCH$_2$C$_6$H$_5$), 5.18 (s, PEGOCH$_2$COOCH$_2$COOC$\underline{H}_2$C$_6$H$_5$), 7.37 (s, PEGOC$\underline{H}_2$COOCH$_2$COOCH$_2$C$_6$H$_5$), 4.24 (s, PEGOCH$_2$C̈OOCH$_2$C̈OOCH$_2$C$_6$H$_5$).

Difunctional carboxymethyl PEG-ester benzyl glycolate 20,000 (3 gram) and Pd/C (10%, 0.8 gram) were added to 30 ml of 1,4-dioxane. The mixture was shaken with $H_2$ (40 psi) at room temperature overnight. The Pd/C was removed by filtration and the solvent was condensed by rotary evaporation. The resulting syrup was added to 100 ml of ether. The precipitated product was collected by filtration and dried in vacuo. Yield 2.4 gram (80%). $^1$H NMR (DMSO-d$_6$): δ 3.5 (br m, PEG), 4.56 (s, PEGCOOC$\underline{H}_2$COOH), 4.20 (s, PEGOC$\underline{H}_2$COOCH$_2$COOH).

Example 3

Preparation of CH$_3$O-PEG-O—(CH$_2$)$_n$—COO—CH$_2$—COONHS

Reactions:

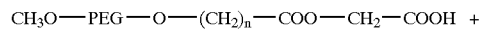

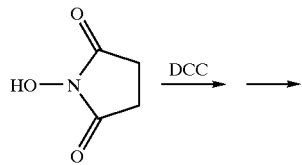

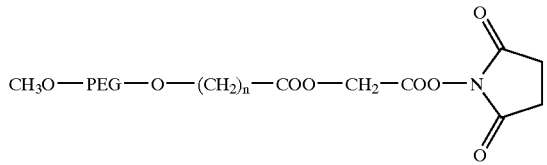

CH$_3$O-PEG-O—(CH$_2$)$_n$—COO—CH$_2$—COOH (1 g, approx. 0.33 mmole) and 42 mg N-hydroxysuccinimide (NHS) (0.35 mmole) was dissolved in 30 ml of dry methylene chloride. To it was added dicyclohexylcarbodiimide (DCC) (80 mg, 0.38 mmole) in 5 ml of dry methylene chloride. The solution was stirred under nitrogen overnight and the solvent was removed by rotary evaporation. The resulting syrup was redissolved in 10 ml of dry toluene and the insoluble solid was filtered off. The solution was then precipitated into 100 ml of dry ethyl ether. The precipitate was collected by filtration and dried in vacuo. Yield 0.95 g (95%). $^1$H NMR (DMSO-d$_6$): δ 3.5 (br m, PEG), 5.15–5.21 (s, PEGCOOC$\underline{H}_2$COONHS), 2.67 (t, PEGOCH$_2$C$\underline{H}_2$COO (PA)), 4.27 (s, PEGOC$\underline{H}_2$COO ppm(CM)), 2.82 (s, NHS, 4 H).

Example 4

Preparation of

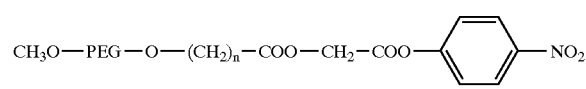

Reactions:

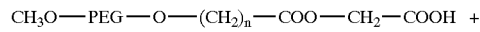

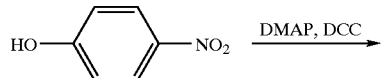

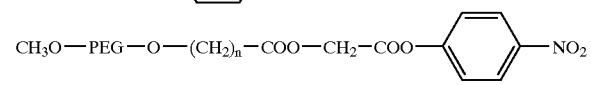

CH$_3$O-PEG-O—(CH$_2$)$_n$—COO—CH$_2$—COOH (1.5 g, approx. 0.5 mmole), 140 mg p-nitrophenol (1 mmole) and 65 mg dimethylaminopyridine (DMAP) (0.525 mmole) were dissolved in 30 ml of dry methylene chloride. To the resulting solution was added dicyclophexylcarbodiimide (DCC) (120 mg, 0.575 mmole) in 5 ml of dry methylene chloride. The solution was stirred under nitrogen overnight and the solvent was removed by rotary evaporation. The resulting syrup was redissolved in 10 ml of dry toluene and the insoluble solid was removed by filtration. Then the solution was precipitated into 100 ml of dry ethyl ether. The product was reprecipitated with ethyl ether, then collected by filtration and dried in vacuo. Yield 1.425 g (95%). $^1$H NMR (DMSO-d$_6$): δ 3.5 (br m, PEG), 5.01 (s, PEGCOOC$\underline{H}_2$COONP), 2.69 (t, PEGOC$\underline{H}_2$CH$_2$COO (PA)), 8.35 & 7.48 (d&d, H$_a$ & H$_b$ in NP, 4H).

Example 5

Preparation of CH$_3$O-PEG-O—(CH$_2$)$_n$—COO—CH(CH$_3$)CH$_2$—COONHS (n=1: mPEG-CM-HBA-NHS and n=2: mPEG-PA-HBA-NHS Reactions:

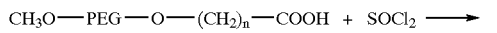

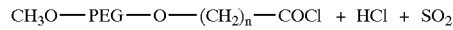

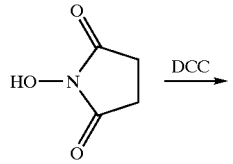

CH$_3$O-PEG-O—(CH$_2$)$_n$—COOH 3000 (3.0 g, 1 mmole) was azeotropically dried with 60 ml of toluene under N$_2$. After two hours, the solution was slowly cooled to room temperature. To the resulting solution was added thionyl chloride solution (3 ml, 6 mmole) in CH$_2$CL$_2$, and the solution was stirred overnight. The solvent was condensed by rotary evaporation and the syrup was dried in vacuo for about four hours over P$_2$O$_5$ powder. 3-hydroxybutyric acid (0.30 g, 2.7 mmole) was azeotropically dried with 70 ml of 1,4-dioxane on a rotary evaporator. The distillation was stopped when approximately 20 ml of solution remained. It was then slowly cooled to room temperature under N$_2$, and the solution was added to the dried PEG acyl chloride. After the PEG was dissolved, 0.6 ml of dry triethylamine was injected to the system (precipitate formed immediately) and the solution was stirred overnight. The salt was removed by filtration and the filtrate was condensed on a rotary evaporator at 55° C. and dried in vacuo. The crude product was then dissolved in 100 ml of distilled water and the pH of the solution was adjusted to 3.0. The aqueous phase was extracted three times with a total of 80 ml of methylene chloride. The organic phase was dried over sodium sulfate, filtered to remove salt, condensed on a rotary evaporator, and added to 100 ml of ethyl ether. The precipitate was collected by filtration and dried in vacuo. Yield 2.76 g (92%). $^1$H NMR (DMSO-d$_6$): δ 3.5 (br m, PEG), 2.54 (d, PEGCOOCH(CH$_3$)C$\underline{H}_2$COOH), 5.1 (h, PEGCOOC$\underline{H}$(CH$_3$)CH$_2$COOH), 1.2 (d, PEG-COOCH(C H$_2$)CH$_2$COOH), 2.54 (t, PEGOCH$_2$CH$_2$COO (PA)), 4.055 (s, PEGOCH$_2$COO (CM)).

mPEG-ester butyric acid NHS ester (CM-HBA-NHS or PA-HBA-NHS): mPEG-ester butyric acid 3000 (1 g, approx., 0.33 mmole, CM-HBA-COOH or PA-HBA-COOH) and 42 mg N-hydroxysuccinimide (NHS) (0.35 mmole was dissolved in 30 ml of dry methylene chloride. To this solution was added dicyclohexylcarbodiimide (DCC) 80 mg, 0.38 mmole) in 5 ml of dry methylene chloride. The solution was stirred under nitrogen overnight and the solvent removed by rotary evaporation. The residual syrup was redissolved in 10 ml of dry toluene and the insoluble solid was removed by filtration. The solution was then precipitated into 100 ml of dry ethyl ether. The precipitate was collected by filtration and dried in vacuo. Yield 0.94 g (94%). $^1$H NMR (DMSO-d$_6$): δ 3.5 (br m PEG), 3.0–3.2 (m, COOCH(CH$_3$)CH$_2$COONHS), 5.26 (h, COOC H(CH$_3$)CH$_2$—COONHS), 1.3 (d, COOCH(C H$_3$)CH$_2$COONHS), 2.54 (t, OCH$_2$CH$_2$COO (PA)), 4.1 (s, OCH$_2$COO (CM)), 2.81 (s, NHS).

Example 6

Determination of Hydrolytic Half-lives of the Ester Linkages

Reactions:

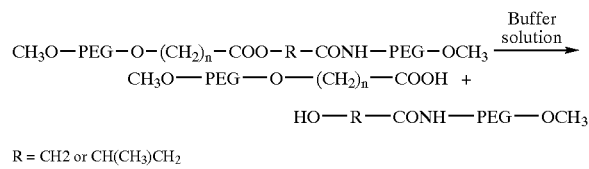

R = CH2 or CH(CH$_3$)CH$_2$

Preparation of CH$_3$O-PEG-O—(CH$_2$)$_n$—COO—CH$_2$—CONH-PEG-OCH$_3$: CH$_3$—O-PEG-O—(CH$_2$)$_n$—COO—CH$_2$—COOH 3000 (0.5 g), 1 equiv. of mPEG-NH$_2$ 2000 and 1 equiv. of 1-hydroxybenzotriazole (HOBT) was dissolved in 50 ml of methylene chloride. To this solution was added one equivalent of dicyclohexylcarbodiimide (DCC) and the solution was stirred at room temperature overnight. The solvent was partially evaporated, the insoluble salt was filtered, and the filtrate was added into a large excess of ethyl ether. The precipitate was collected by filtration and dried in vacuo. Yield: 0.8 g (95%). $^1$H MNR (DMSO-d$_6$): δ 3.5 (br m, PEG), 2.34 (t, —CONHCH$_2$CH$_2$—O-PEG-).

Determination of hydrolytic half-lives of PEG ester conjugates with PEG amine: The conjugates from the above step and 20 wt % PEG 20,000 (as internal standard) were dissolved in a buffer solution. Then the concentration of the conjugate (C) and its hydrolysis product were monitored by HPLC-GPC (Ultrahydrogel 250 column, 7.8×300 mm, Waters) at predetermined time. The hydrolytic half-lives were obtained from the slope of the natural logarithm of C at the time t minus C at infinite time versus time, assuming $1^{st}$ order kinetics.

TABLE 1

Hydrolysis Half-Lives (days, unless noted otherwise) of the Ester Linkages Formed Between 1 and mPEG Amine (±10%)

| | Double-Ester PEG Used | | | | | | |
|---|---|---|---|---|---|---|---|
| | CM-GA | PA-GA | | CM-HBA | | PA-HBA | |
| pH | 7.0 | 7.0 | 8.1 | 7.0 | 8.1 | 7.0 | 8.1 |
| 23° C. | 3.2 | 43 | 6.5 | — | 15 | — | 120 |
| 37° C. | 14 h | 7.6 | — | 14 | — | 112 | — |
| 50° C. | 4 h | 2.2 | — | 5 | — | 58 | — |

Example 7

Determination of Hydrolysis Half-lives of the Active Ester

Reactions:

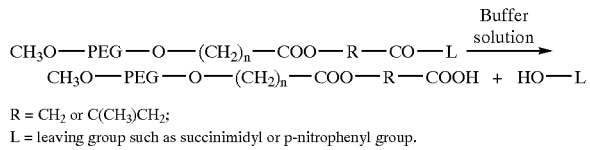

R = CH$_2$ or C(CH$_3$)CH$_2$;
L = leaving group such as succinimidyl or p-nitrophenyl group.

Determination of hydrolysis half-lives of PEG active ester: Measurements were conducted using a HP8452a UV-VIS spectrophotometer. In an experiment, 1 mg PEG active ester was dissolved in 3.0 ml of buffer solution and shaken promptly to obtain solution as soon as possible. Then the solution was transferred into an UV cuvette and the absorbance at 260 nm for NHS ester or at 402 nm for the p-nitrophenyl ester was followed as a function of time. The hydrolytic half life was determined from the first order kinetic plot (natural logarithm of final absorbance minus absorbance at the time t versus time).

TABLE 2

Hydrolysis Half-Lives of Succinimidyl Active Esters (R = NHS) and p-nitrophenyl Active Esters (R = NP) of PEG-ester Acids at pH 8.1 and Room Temperature

| R | CM-GA-R | PA-GA-R | CM-HBA-R | PA-HBA-R |
|---|---|---|---|---|
| NHS | 11 s | 11 s | 12 min | 12 min |
| NP | 7 min | 7 min | — | — |

Example 8

Monitoring Hydrolytic Release of the PEG from its Protein Conjugate by MALDI-TOF Mass Spectrometry Modification of subtilisin with the PEG: To a subtilisin solution (1 ml, 2 mg/ml in 0.2M boric buffer pH 8.0) was added 15 mg mPEG-CM-HBA-NHS 3000. The solution was placed in an automatic shaker at room temperature. At predetermined time periods, 50 μl of the solution was removed and preserved in a refrigerator for MALDI-TOF MS measurement.

MALDI spectra was measured on a PerSeptive Biosystems' Voyager linear time-of-flight instrument. Briefly, a nitrogen laser lamda=337 nm, 10 ns pulse width) was used to generate ions which were extracted with a potential of 30 kV. Ions drifted through a 1.3 m drift tube and were monitored in positive ion mode.

Figure 2:
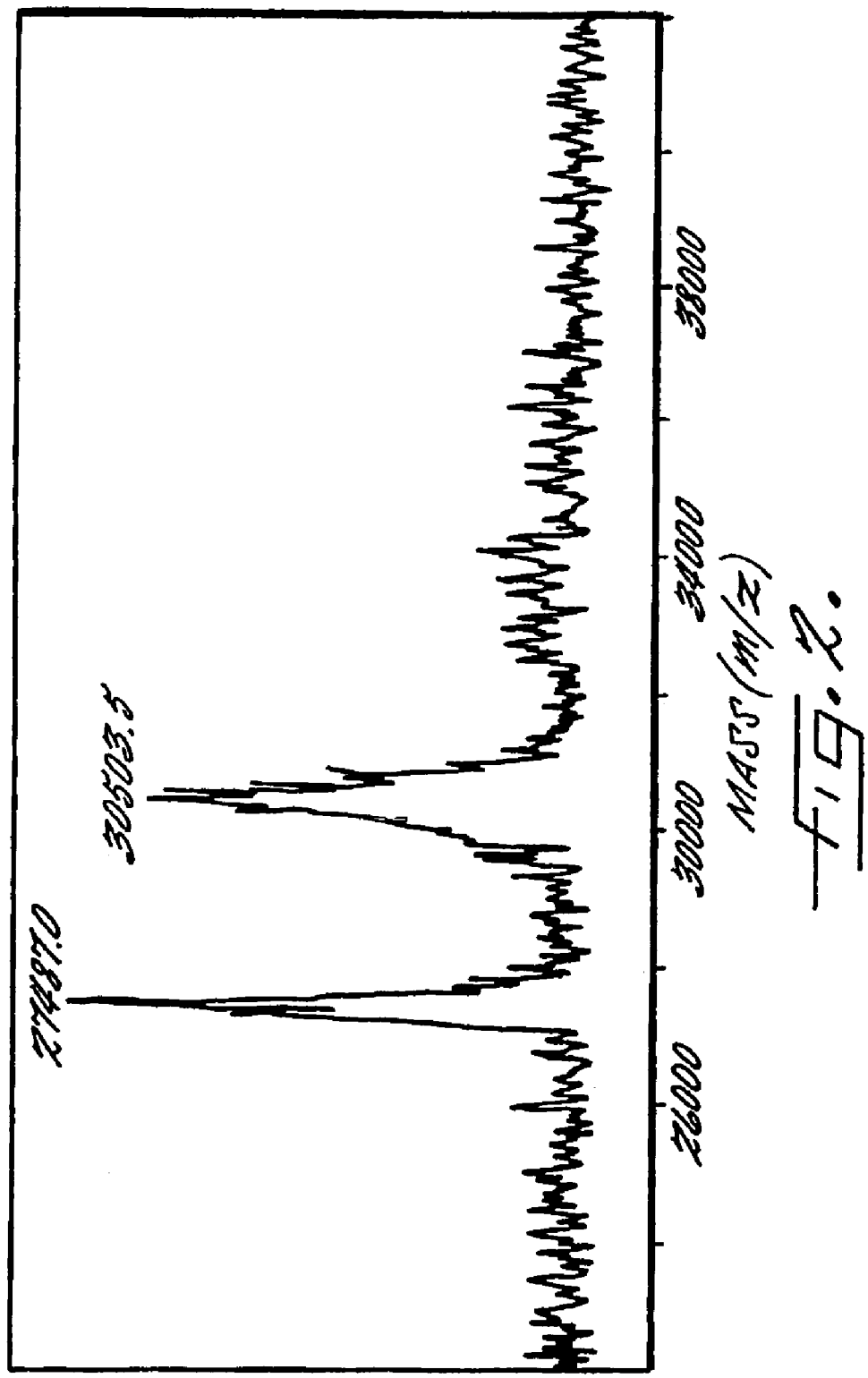
Figure 3:
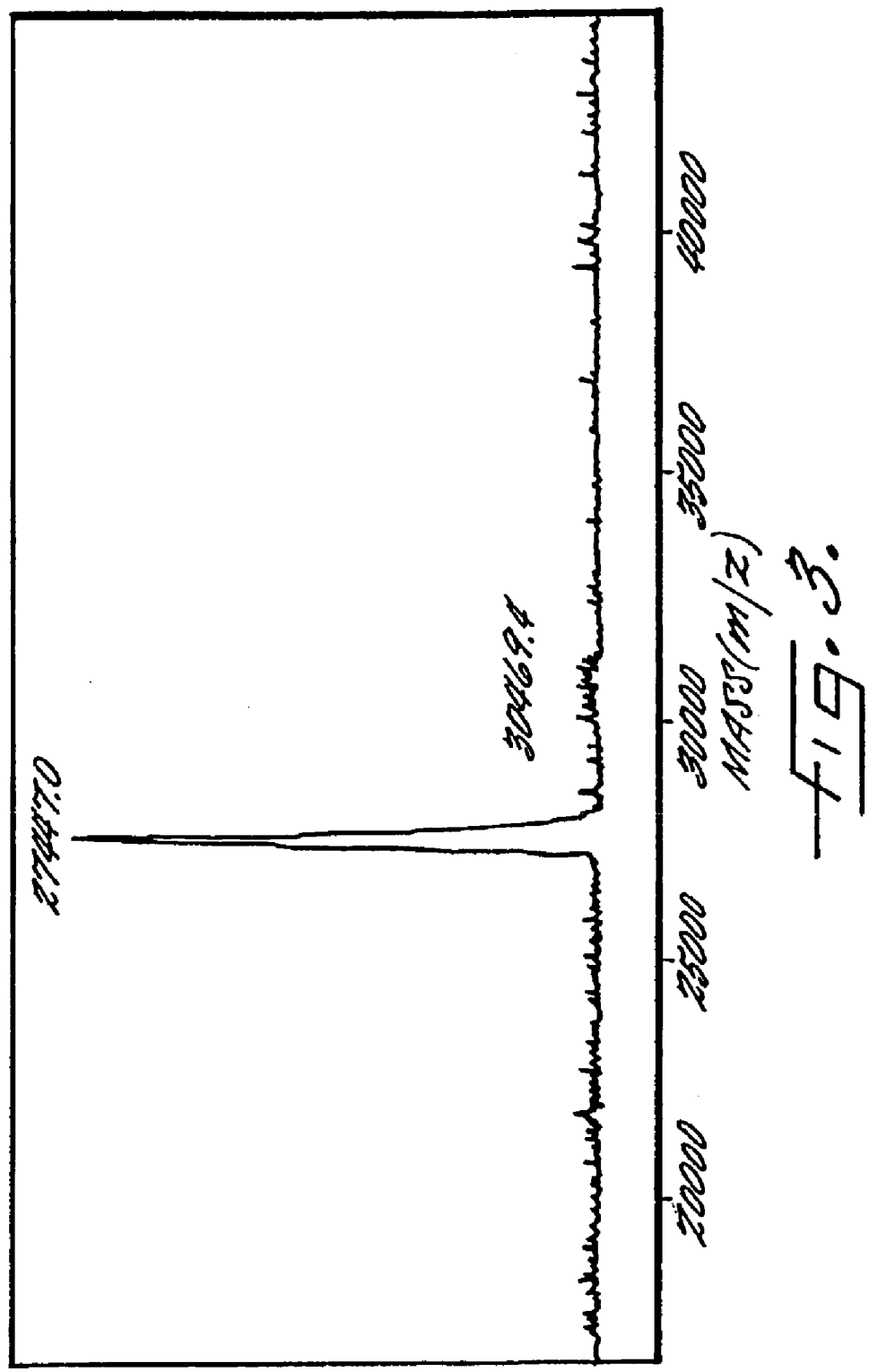

Protein samples were dissolved in deionized H₂O or 50 mM NaCl solution to a concentration of approximately 10 pmol/μl. The matrix, 3,5-dimethoxy-4-hydroxycinnamic acid (sinapinic acid), was dissolved in a 80:20 by volume ratio of acetonitrile to deionized water at a concentration of 10 mg/ml. 1 μl of the solution was deposited on the sample plate and then mixed with 1 μl of matrix solution. The sample was allowed to crystallize by solvent evaporation under ambient conditions. MALDI-MS spectra of the molecular weight distribution of the mPEG-HBA and subtilisin conjugate are shown in FIGS. 1 through 3 for different times after preparation. FIG. 1 is 1 day. FIG. 2 is 8 days. FIG. 3 is 14 days.

Example 9

Preparation of

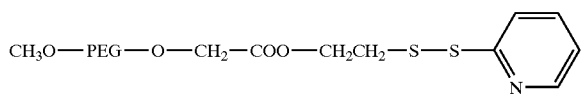

Reactions:

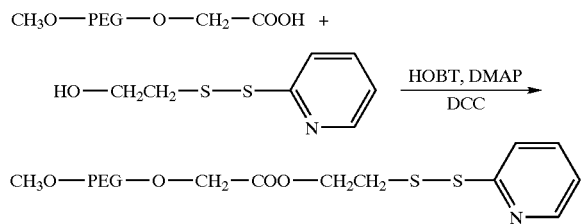

CH₃O-PEG-O—CH₂—COOH 5000 (3.0 g, 0.6 mmole), 2-(2-pyridyldithio)ethanol (342 mg, 1.5 mmole), DMAP (180 mg, 1.44 mmole) and HOBT (93 mg, 0.61 mmole) were dissolved in 60 ml of dichloromethane. To this solution was added DCC (138 mg, 0.66 mmole) in 5 ml of dichloromethane. The solution was stirred at room temperature under N₂ overnight. The solvent was removed by rotary evaporation and 15 ml of toluene was added to the residue. After all PEG dissolved, the solution was filtered to remove dicyclohexyl urea. To the solution was added 45 ml of methylene chloride and the solution was washed with sodium acetate buffer (0.1M, pH 5.0) which contained 10% sodium chloride. The organic phase was dried over anhydrous sodium sulfate, filtered to remove salt, condensed on a rotary evaporator, and precipitated into 100 ml of ethyl ether. The product was collected by filtration and dried in vacuo. Yield 2.85 g (95%). ¹H NMR (DMSO-d₆): δ 3.5 (br m, PEG), 4.11 (s, PEGOC$\underline{H}$₂COO—), 4.30 (t, COOC$\underline{H}$₂CH₂SS-) 7.29 (t, one aromatic proton), 7.77 (t+d, two aromatic protons), 8.46 (d, one aromatic proton).

Example 10

Determination of Hydrolysis Half-Lives of the Ester Linkage

Reactions:

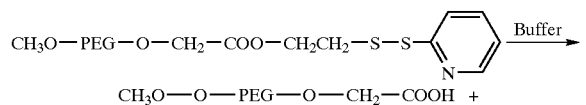

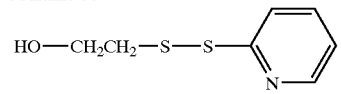

mPEG-CM-SSP and 20% PEG 20,000 (wt) (as internal standard) were dissolved in 10 mM phosphate buffer (pH 7.2) and a series of ampoules were sealed each containing about 0.25 ml of above solution. The ampoules were stored as two groups, one group at room temperature and the other at 37° C. At each measurement, one ampoule in each group was opened and the solution was analyzed. The concentration of mPEG-CM-SSP and its hydrolysis product were determined by HPLC-GPC (Ultrahydrogel 250 column, Waters; 5 mM phosphate bufer pH 7.2 as mobile phase). The hydrolytic half-life was obtained from the slope of the natural logarithm of C at the time t minus C at infinite time versus time, assuming 1st order kinetics.

TABLE 3

| Hydrolytic Half-Lives (Days) of the Ester in mPeg-CM-SSP (±10%) | | |
|---|---|---|
| | pH 5.5 | pH 7.0 |
| Room temperature | 107 | 18 |
| 37° C. | 20 | 2.9 |

Example 11

Preparation of CH₃O-PEG-O(CH₂)n-CO₂-PEG-OCOONHS

Reactions:

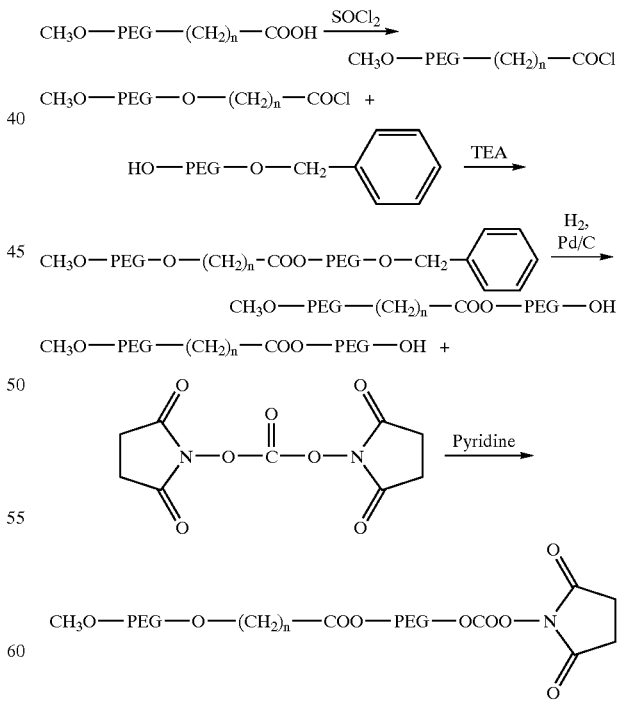

(a) Preparation of CH₃O-PEG-OCH₂CH₂CO₂-PEG-OBz

In a 100 ml round-bottom flask, a solution of CH₃O-PEG-O—(CH₂)ₙ—CO₂H (MW=2000, 2 g, 1 mmol) was dissolved in toluene and azeotropically dried for two hours.

After slowly cooling to room temperature, the solution was added to thionyl chloride (3 ml, 6 mmole) in methylene chloride and then stirred under $N_2$ overnight. The solvent was then removed by rotary evaporation and the residual syrup was dried in vacuo for about four hours over $P_2O_5$ powder. To the solid was added 5 ml of anhydrous methylene chloride and A solution (20 ml) (of azeotropically dried BzO-PEG-OH (MW=3400, 2.04 g, 0.60 mmol) in toluene To the resulting solution was added 0.6 ml of freshly distilled triethylamine and the solution was stirred overnight. The triethylamine salt was removed by filtration and the crude product was precipitated with ethyl ether and collected by filtration. The mixture was then purified by ion-exchange chromatography (DEAE sepharose fast flow column, Pharmacia). Pure $CH_3$O-PEG-O—$(CH_2)_n$—$CO_2$-PEG-OBz was obtained. Yield: 2.6 g (80%). NMR (DMSO-$d_6$): δ 3.5 (br m, PEG), 2.55 (t, —OC$H_2$C$H_2$COOPEG-), 4.14 (s, -PEGOC$H_2$COOPEG-), 4.13 (t, -PEGOC$H_2$C$H_2$—COOC$H_2$C$H_2$OPEG-), 4.18 (t, -PEGOC$H_2$—COOC$H_2$C$H_2$OPEG), 4.49 (s, -PEG-O—C$H_2$—$C_6H_5$), 7.33 (s+com, -PEG-O—$CH_2$—$C_6\underline{H}_5$).

(b) Preparation of $CH_3$O-PEG-O—$(CH_2)_n$—$CO_2$-PEG-OH

A solution of 2 g of $CH_3$O-PEG-O—$(CH_2)_n$—$CO_2$-PEG-OBz in 1,4-dioxane was hydrogenolyzed with $H_2$ (2 atm) on 1 gram Pd/C (10%) overnight. The catalyst was removed by filtration, the solvent was condensed under vacuum and the solution was added to ethyl ether. The product was collected by filtration and dried under vacuum at room temperature to yield: 1.5 g (75%) of $CH_3$O-PEG-O—$(CH_2)_n$—$CO_2$-PEG-OH. NMR (DMSO-$d_6$): δ 3.5 (br m, PEG), 2.55 (t, —OCH$_2$C$H_2$COOPEG-), 4.14 (s, -PEG-OC$H_2$COOPEG-), 4.13 (t, -PEGOCH$_2$CH$_2$COOC$H_2$CH$_2$OPEG-), 4.18 (t, -PEGOCH$_2$—COOC$H_2$C$H_2$OPEG).

(c) Preparation of $CH_3$O-PEG-O—$(CH_2)_n$—$CO_2$-PEG-OCOONHS $CH_3$O-PEG-O—$(CH_2)_n$—$CO_2$-PEG-OH 5400 (1.25 g, 0.23 mmole) was azeotropically distilled with 100 ml acetonitrile and then cooled to room temperature. To it were added disuccinimidyl carbonate (245 milligram, 0.92 mmole) and 0.1 ml of pyridine, and the solution was stirred at room temperature overnight. The solvent was then removed under vacuum, and the resulting solid was dissolved in 35 ml of dry methylene chloride. The insoluble solid was removed by filtration, and the filtrate was washed with pH 4.5 sodium chloride saturated acetate buffer. The organic phase was dried over anhydrous sodium sulfate, filtered, condensed by rotary evaporation, and precipitated into ethyl ether. The product was collected by filtration and dried in vacuo. Yield: 1.20 g (96%), 100% substitution of succimidyl carbonate and no reagent left. NMR (DMSO-$d_6$): δ 3.5 (br m, PEG), 2.55 (t, —OC$H_2$CH$_2$COOPEG-), 4.14 (s, -PEG-OC$H_2$COOPEG-), 4.13 (t, -PEGOCH$_2$CH$_2$COOC$H_2$CH$_2$OPEG-), 4.18 (t, -PEGOCH$_2$—COOC$H_2$C$H_2$OPEG), 4.45 (t, -PEGO-CH$_2$C$H_2$OCONHS), 2.81 [s, NHS].

The invention has been described in particular exemplified embodiments. However, the foregoing description is not intended to limit the invention to the exemplified embodiments and the skilled artisan should recognize that variations can be mad within the scope and spirit of the invention as described in the foregoing specification. On the contrary, the invention includes all alternatives, modifications, and equivalents that may be included within the true spirit and scope of the invention as defined by the appended claims.

That which is claimed is:

1. A conjugate, comprising:
a water-soluble and non-peptidic polymer covalently attached to the structure:

—W—X—P wherein:

P is a biologically active molecule;

W is selected from the group consisting of —O—C(O)—$(CH_2)_n$—O—, —O—$(CH_2)_n$—C(O)—O—$(CH_2)_m$—, —O—$(CH_2)_n$—C(O)—O—$(CH_2)_m$—O—, —$(CH_2)_n$—OPO$_3$—$(CH_2)_m$—, and —O—$(CH_2)_n$—C(O)—O—(CHR)$_m$—, wherein each R is H or alkyl, provided at least one R is alkyl, n and m each independently range from about 1 to about 5; and X is a covalent linkage.

2. A conjugate according to claim 1, wherein n and m are each independently 1 or 2.

3. A conjugate according to claim 2, wherein n is 1 and m is 2.

4. A conjugate according to claim 1, wherein W is —O—$(CH_2)_n$—C(O)—O—$(CH_2)_m$—.

5. A conjugate according to claim 1, wherein W is —O—$(CH_2)_n$—C(O)—O—(CHR)$_m$.

6. A conjugate according to claim 1, wherein W is —O—CH$_2$—C(O)—O—CH(CH$_3$)—CH$_2$—.

7. A conjugate according to claim 1, wherein W is —O—CH$_2$—C(O)—O—CH$_2$—CH$_2$—.

8. A conjugate according to claim 1, wherein said polymer is selected from the group consisting of poly(alkylene oxides), poly(vinyl alcohol), poly(oxyethylated polyols), poly(vinyl pyrrolidone), poly(oxazoline), poly(acryloylmorpholine), and copolymers or terpolymers thereof.

9. A conjugate according to claim 1, wherein said polymer is a linear or a branched poly(ethylene glycol).

10. A conjugate according to claim 9, wherein said poly(ethylene glycol) has a molecular weight of about 300 to about 100,000 daltons.

11. A conjugate according to claim 9, wherein said poly(ethylene glycol) is end-capped.

12. A conjugate according to claim 1, wherein said polymer is a linear poly(ethylene glycol) having two termini, wherein the terminus opposite —W—X—P is selected from the group consisting of hydroxy, alkoxy, and —W'-X'—P', wherein W', X', and P' are the same as W, X and P, respectively.

13. The conjugate according to claim 12, having the structure:

P'—X'—W'-POLY-W—X—P, wherein

POLY corresponds to —CH$_2$CH$_2$—O—(CH$_2$CH$_2$O)$_n$—CH$_2$CH$_2$—, n ranges from about 10 to about 2000, and W and W' are both either —O—$(CH_2)_n$—C(O)—O—$(CH_2)_m$— or —O—$(CH_2)_n$—C(O)—O—(CHR)$_m$—.

14. The conjugate of claim 12, having the structure:

Z-POLY-W—X—P, wherein

Z is selected from the group consisting of —OH, —OCH$_3$, and —W'—X'—P',

POLY corresponds to —CH$_2$CH$_2$—O—(CH$_2$CH$_2$O)$_n$—CH$_2$CH$_2$—, and n ranges from 10 to about 2000.

15. A conjugate according to claim 1, wherein said polymer is a linear or a branched poly(ethylene glycol), and W is —O—$(CH_2)_n$—C(O)—O—$(CH_2)_m$— or —O—$(CH_2)_n$—C(O)—O—(CHR)$_m$—.

16. A conjugate according to claim 1, wherein X i selected from the group consisting of amide, urethane, and urea.

17. A conjugate according to claim 1, wherein X is formed by reaction of Y and T, wherein Y is a reactive group on the biologically active molecule and T is a reactive group on the polymer selected from the group consisting of ester, isocyanate, aldehyde, epoxide, and sulfonate ester.

18. A conjugate according to claim 1, wherein P is elected from the group consisting of amino acids, enzymes, peptides, proteins, oligonucleotides and small drug molecules.

19. A conjugate according to claim 1, having the structure:

$$CH_3-O-PEG-O-(CH_2)_n-C(O)-O-(CH_2)_m-X-P.$$

20. A conjugate according to claim 19, wherein X selected from the group consisting of amide, urethane, and urea.

21. A conjugate according to claim 1, having the structure:

$$CH_3-O-PEG-O-CH_2-C(O)-O-CH(CH_3)CH_2-X-P.$$

22. A conjugate according to claim 21, wherein X is selected from the group consisting of amide, urethane, and urea.

23. A conjugate according to claim 1, having the structure:

$$P-X-(CH_2)_m-O-C(O)-(CH_2)_n-O-PEG-O-(CH_2)_n-C(O)-O-(CH_2)_m-X-P \text{ or}$$

$$P-X-CH_2-CH(CH_3)-O-C(O)-CH_2-O-PEG-O-CH_2-C(O)-O-CH(CH_3)-CH_2-X-P.$$

24. A conjugate according to claim 23, wherein X is selected from the group consisting of amide, urethane, and urea.

25. A conjugate according to claim 1, having the structure:

$$CH_3-O-PEG-O-(CH_2)_n-C(O)-O-(CHR)_m-X-P.$$

26. A conjugate according to claim 25, wherein X is selected from the group consisting of amide, urethane, and urea.

27. A conjugate according to claim 1, having the structure:

$$P-X-(CHR)_m-O-C(O)-(CH_2)_n-O-PEG-O-(CH_2)_n-C(O)-O-(CHR)_m-X-P.$$

28. A conjugate according to claim 27, wherein X is selected from the group consisting of amide, urethane, and urea.

29. A conjugate, comprising a poly(ethylene glycol) covalently attached to the structure:

$$-W-X-P$$

wherein:
P represents a surface or a biologically active molecule selected from the group consisting of amino acids, enzymes, peptides, proteins, oligonucleotides, and small drug molecules;
W is selected from the group consisting of $-O-C(O)-(CH_2)_n-O-$, $-O-(CH_2)_n-C(O)-O-(CH_2)_m-$, $-O-(CH_2)_n-C(O)-O-(CH_2)_m-O-$, $-(CH_n)_n-OPO_3-(CH_2)_m-$, and $-O-(CH_2)_n-C(O)-O-(CHR)_m-$, wherein each R is H or alkyl, provided at least one R is alkyl, n and m each independently range from about 1 to about 5; and
X is a covalent linkage.

30. A conjugate according to claim 29, wherein is formed by reaction of Y and T, wherein Y is a reactive group on the biologically active molecule and T is a reactive group on the poly(ethylene glycol) selected from the group consisting of ester, isocyanate, aldehyde, epoxide, and sulfonate ester.

31. A conjugate according to claim 29, wherein X is selected from the group consisting of amide, urethane, and urea.

32. A conjugate formed by reaction of a biologically active molecule or a surface with a water-soluble and non-peptidic polymer, where the polymer comprises the structure:

POLY-W-T wherein
POLY is a linear or a branched water-soluble and non-peptidic polymer segment
W is selected from the group consisting of $-O-C(O)-(CH_2)_n-O-$, $-O-(CH_2)_n-C(O)-O-(CH_2)_m-$, $-O-(CH_2)_n-C(O)-O-(CH_2)_m-O-$, $-(CH_2)_n-OPO_3-(CH_2)_m-$, and $-O-(CH_2)_n-C(O)-O-(CHR)_m-$, wherein each R is H or alkyl, provided at least one R is alkyl, n and m each independently range from about 1 to about 5; and
T is a reactive group.

33. A conjugate according to claim 32, wherein W is $-O-(CH_2)_n-C(O)-O-(CH_2)_m$.

34. A conjugate according to claim 32, wherein W is $-O-(CH_2)_n-C(O)-O-(CHR)_m-$.

35. A conjugate according to claim 32, wherein W is $-O-CH_2-CO_2-CH(CH_3)-CH_2-$.

36. A conjugate according to claim 32, wherein POLY is selected from the group consisting of poly(alkylene oxides), poly(vinyl alcohol), poly(oxyethylated polyols), poly(vinyl pyrrolidone), poly(oxazoline) and poly(acryloylmorpholine).

37. A conjugate according to claim 32, wherein POLY is poly(ethylene glycol).

38. A conjugate according to claim 32, wherein POLY is a linear poly(ethylene glycol) having two termini, wherein the terminus opposite $-W-T$ is selected from the group consisting of hydroxy, alkoxy, and $-W'-T'-$, wherein W' and T' are the same as W and T, respectively.

39. A conjugate according to claim 32, wherein POLY is poly(ethylene glycol) and T is selected from the group consisting of $-COOH$, a carboxylate ester, or a carbonate ester.

40. A conjugate according to claim 32, wherein T is $-CO_2-$ succinimidyl.

41. A conjugate according to claim 32, wherein T is selected from the group consisting of active esters, aldehydes, ketones, isocyanates, isothiocyanates, epoxides, alcohols, amines, and thiols.

42. A conjugate according to claim 32, wherein T is selected from the group consisting of $-COOH$, $-N=C=O$, $-CO_2$-succinimidyl, $-CO_2$-benzotriazole, $-CO_2$-sulfosuccinimidyl, $-CO_2$-p-nitrophenyl, and pyridyldisulfide.

43. A conjugate according to claim 32, wherein W is $-O-(CH_2)_n-C(O)-O-(CH_2)_m-$ or $-O-(CH_2)_n-C(O)-O-(CHR)_m-$; and T is selected from the group consisting of $-COOH$, $-N=C=O$, $-CO_2$-succinimidyl, $-CO_2$-benzotriazole, $-CO_2$-sulfosuccinimidyl, $-CO_2$-p-nitrophenyl, and pyridyldisulfide.

44. A conjugate according to claim 32, wherein POLY-W-T is selected from the group consisting of:

$$CH_3-O-PEG-O-(CH_2)_n-C(O)-O-(CH_2)_m-COOH;$$

$$HO-PEG-O-(CH_2)_n-C(O)-O-(CH_2)_m-COOH;$$

$$HOOC-(CH_2)_m-O-C(O)-(CH_2)_n-O-PEG-O-(CH_2)_n-C(O)-O-(CH_2)_m-COOH;$$

$$CH_3-O-PEG-O-(CH_2)_n-C(O)-O-(CH_2)_m-C(O)-O-NHS;$$

HO-PEG-O—(CH$_2$)$_n$—C(O)—O—(CH$_2$)$_m$—C(O)—O-NHS;

NHS-O—(O)—C(CH$_2$)$_m$—O—C(O)—(CH$_2$)$_n$—O-PEG-O—(CH$_2$)$_n$—C(O)—O—(CH$_2$)$_m$—C(O)—O-NHS;

CH$_3$—O-PEG-O—(CH$_2$)$_n$—C(O)—O—(CH$_2$)$_m$—C(O)—O-p-nitrophenyl;

p-nitrophenyl-O—C(O)—(CH$_2$)$_m$—O—C(O)—(CH$_2$)$_n$—O-PEG-O—(CH$_2$)$_n$—C(O)—O—(CH$_2$)$_m$—C(O)—O-p-nitrophenyl;

CH$_3$—O-PEG-O—(CH$_2$)$_n$—C(O)—O—(CHR)$_m$—C(O)—O-NHS;

HO-PEG-O—(CH$_2$)$_n$—C(O)—O—(CHR)$_m$—C(O)—O-NHS

NHS-O—C(O)—(CHR)$_m$—O—C(O)—(CH$_2$)$_n$—O-PEG-O—(CH$_2$)$_n$—C(O)—O—(CHR)$_m$—C(O)—O-NHS;

CH$_3$—O-PEG-O—(CH$_2$)$_n$—C(O)—O—(CH$_2$)$_m$-pyridyldisulfide;

pyridyldisulfide-(CH$_2$)$_m$—O—C(O)—(CH$_2$)$_n$—O-PEG-O—(CH$_2$)$_n$—C(O)—O—(CH$_2$)$_m$-pyridyldisulfide;

CH$_3$—O-PEG-O—C(O)—(CH$_2$)$_n$—O—C(O)—O-NHS;

HO-PEG-O—C(O)—(CH$_2$)$_n$—O—C(O)—O-NHS, and

NHS-O—C(O)—O—(CH$_2$)$_n$—C(O)—O-PEG-O—C(O)—(CH$_2$)$_n$—O—C(O)—O-NHS, wherein NHS is succinimidyl.

* * * * *

UNITED STATES PATENT AND TRADEMARK OFFICE
CERTIFICATE OF CORRECTION

PATENT NO. : 6,864,350 B2
DATED : March 8, 2005
INVENTOR(S) : J. Milton Harris

It is certified that error appears in the above-identified patent and that said Letters Patent is hereby corrected as shown below:

Column 3,
Line 13, after "conjugate" delete "d" and insert -- and --;

Column 16,
Line 66, after "wherein X" delete "i" and insert -- is --;

Column 17,
Line 8, after the word "oligonucleotides" insert a comma -- , --;
Line 54, "$(CH_n)_n$" should read -- $(CH_2)_n$ --;
Line 60, after "wherein" insert -- X --;

Column 18,
Line 42, replace "claim 32" with -- claim 39 --;

Column 19,
Line 3, after "NHS—O—" insert -- C --.

Signed and Sealed this

Seventeenth Day of May, 2005

JON W. DUDAS
*Director of the United States Patent and Trademark Office*